US008757149B2

(12) United States Patent
Kirniak

(10) Patent No.: US 8,757,149 B2
(45) Date of Patent: *Jun. 24, 2014

(54) DEVICE FOR DISPENSING A FLUID PRODUCT

(75) Inventor: Maxime Kirniak, Rouen (FR)

(73) Assignee: Aptar France SAS, Le Neubourg (FR)

( * ) Notice: Subject to any disclaimer, the term of this patent is extended or adjusted under 35 U.S.C. 154(b) by 848 days.

This patent is subject to a terminal disclaimer.

(21) Appl. No.: 12/988,266

(22) PCT Filed: Apr. 10, 2009

(86) PCT No.: PCT/FR2009/050644
§ 371 (c)(1),
(2), (4) Date: Oct. 15, 2010

(87) PCT Pub. No.: WO2009/136097
PCT Pub. Date: Nov. 12, 2009

(65) Prior Publication Data
US 2011/0048419 A1    Mar. 3, 2011

(30) Foreign Application Priority Data
Apr. 16, 2008  (FR) ..................... 08 52544

(51) Int. Cl.
*A61M 15/00*    (2006.01)
(52) U.S. Cl.
USPC ............ 128/203.15; 128/200.24; 128/203.12; 128/200.23; 128/203.21
(58) Field of Classification Search
None
See application file for complete search history.

(56) References Cited

U.S. PATENT DOCUMENTS

| 5,823,178 | A  | * | 10/1998 | Lloyd et al. | 128/200.14 |
| 6,725,857 | B2 | * | 4/2004  | Ritsche      | 128/200.14 |
| 7,424,888 | B2 | * | 9/2008  | Harvey et al.| 128/203.15 |
| 7,434,579 | B2 | * | 10/2008 | Young et al. | 128/203.15 |
| 2005/0005934 | A1 |  | 1/2005 | Harvey |  |
| 2005/0039743 | A1 |  | 2/2005 | Taylor |  |
| 2005/0268909 | A1 | * | 12/2005 | Bonney et al. | 128/203.15 |
| 2006/0196504 | A1 | * | 9/2006  | Augustyn et al. | 128/203.15 |
| 2007/0137645 | A1 | * | 6/2007  | Eason et al. | 128/203.12 |
| 2008/0127973 | A1 |  | 6/2008 | Pocock et al. |  |
| 2008/0163868 | A1 |  | 7/2008 | Pocock et al. |  |

FOREIGN PATENT DOCUMENTS

| FR | 2 881 118 A1 | 7/2006 |
| WO | 2008/012458 A2 | 1/2008 |

* cited by examiner

*Primary Examiner* — Jackie T Ho
*Assistant Examiner* — Eric Bryant
(74) *Attorney, Agent, or Firm* — Sughrue Mion, PLLC

(57) ABSTRACT

A fluid dispenser device including a body (10), an elongate flexible strip (20) supporting a plurality of reservoirs (21), a reservoir opening mechanism (30); a first displacement mechanism (40) for causing the flexible strip to advance so as to bring a full reservoir into register with the reservoir-opening mechanism; and a second displacement mechanism (45) for displacing a reservoir (21) against the reservoir opening mechanism (30). The leading end (25) of the flexible strip (20), in the advance direction of the strip is fastened to a receiver element (50), which is displaceable on a path along a guide mechanism (100), between a first position that corresponds to the first actuation of the device and a second position that corresponds to the last actuation of the device.

20 Claims, 1 Drawing Sheet

DEVICE FOR DISPENSING A FLUID PRODUCT

The present invention relates to a fluid dispenser device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. Another problem that exists with inhalers provided with blister strips is associated with the movement of the strip, and with storage of the used portion of the strip. Thus, depending on the length of the strip, a large space can turn out to be necessary, and any blockage of the blister strip can prevent the inhaler from functioning properly. In addition, when the device for advancing the strip pulls simultaneously on the leading end of the strip so as to avoid poor rolling up, a problem can occur over successive actuations, in particular because the diameter of the rolled-up used strip increases progressively.

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide such an inhaler provided with a blister strip, in which inhaler, storage of the used strip portion is optimized, and the risk of the strip blocking is minimized.

The present invention thus provides a fluid dispenser device comprising: a body; an elongate flexible strip supporting a plurality of reservoirs each containing a dose of fluid or powder; reservoir-opening means for opening a respective reservoir on each actuation; first displacement means for causing said flexible strip to advance before and/or during and/or after each actuation, so as to bring a full reservoir into register with said reservoir-opening means; and second displacement means for displacing a full reservoir against said opening means each time the device is actuated, the leading end of said flexible strip, in the advance direction of said strip, being fastened to a receiver element, said receiver element being displaceable, on a path along guide means, between a first position that corresponds to the first actuation of the device and a second position that corresponds to the last actuation of the device.

Advantageously, said receiver element is also rotatably mounted.

Advantageously, said receiver element is fastened to a stressed spring that is adapted to exert a force on said receiver element so as to urge it to turn, such that said receiver exerts a traction force on said elongate strip, said traction force being independent of said first and second displacement means.

Advantageously, said traction force is at a maximum when the device is first used and reduces on each actuation as the spring relaxes.

Advantageously, said spring is a spiral spring, a leaf spring, or a helical spring.

Advantageously, said spring is fastened firstly to a fastener pin that cannot turn, and secondly to said rotary receiver element.

Advantageously, said guide means include a slot in which the receiver element can slide.

Advantageously, said guide means are substantially rectilinear.

Advantageously, said receiver element is displaced along said guide means each time the device is actuated.

Advantageously, said receiver element is mounted on a support surface, preferably by means of snap-fastener studs, so as to fasten said receiver element both axially and transversally relative to said support surface, while enabling it to turn about its axis of rotation, said support surface sliding along said guide means.

Advantageously, said receiver element is rotatably fastened on a support surface that is secured to said second displacement means, said support element being displaced in rotation each time the device is actuated, together with the reservoir to be opened.

Advantageously, said opening means comprise a needle that does not move relative to said body, a reservoir being displaced against said needle each time the device is actuated, said needle penetrating into said reservoir so as to empty it by means of an inhalation flow.

Advantageously, said opening means are controlled by the user inhaling, such that the reservoir is opened and emptied simultaneously by said inhalation flow.

These characteristics and advantages and others of the present invention appear more clearly from the following detailed description, given by way of non-limiting example, and with reference to the accompanying drawings, and in which.

Figure 1:
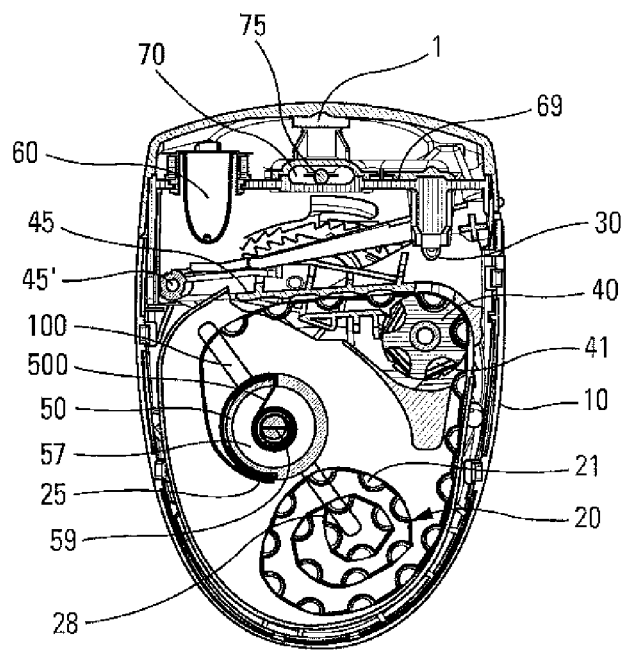
FIG. 1 is a diagrammatic section view showing a dispenser device constituting an advantageous embodiment of the invention.

FIG. 1 shows an advantageous variant embodiment of a dry-powder inhaler. The inhaler includes a body 10 on which there can be slidably mounted two cap-forming portions (not shown) that are adapted to be opened so as to open and load the device. The body 10 can be approximately rounded in shape, as shown in the figures, but it could be of any other appropriate shape. The body 10 includes a mouthpiece or inhaler endpiece 1 that defines a dispenser orifice through which the user inhales while the device is being actuated. The caps can be opened by pivoting about a common pivot axis, but any other opening means can be envisaged for opening the device. In a variant, the device could include a single cover instead of two.

Inside the body 10 there is provided a strip 20 of individual reservoirs 21, also known as blisters, said strip being made in the form of an elongate flexible strip 20 on which the blisters 21 are disposed one behind another, in manner known per se. The blisters 21, preferably containing powder, are not shown in FIGS. 2 and 3, so as to avoid cluttering the drawings for the purpose of clarity. The blister strip 20 is advantageously constituted by a base layer or wall that forms the cavities receiving the doses of powder, and by a closure layer or wall that covers each of said blisters 21 in sealed manner. Before first use, the blister strip 20 can be rolled-up inside the body 10, preferably in a storage portion, and first displacement means 40 for displacing the strip are provided for progressively unrolling the blister strip and for causing it to advance. Second displacement means 45 are provided for bringing a respective blister or individual reservoir 21 into a dispensing position each time the device is actuated. The strip portion including the empty reservoirs is advantageously adapted to be rolled-up at another location of said body 10, preferably a reception portion, as described in greater detail below.

The inhaler includes reservoir opening means 30 preferably comprising perforator and/or cutter means for perforating and/or cutting the closure layer of the blisters. For example, the reservoir opening means advantageously comprise a needle 30 that is preferably stationary relative to the body 10, and against which a respective blister 21 is displaced on each actuation by the second displacement means 45. The blister is thus perforated by said needle which penetrates into said blister so as to expel the powder by means of the suction of the user inhaling.

The first displacement means 40 are adapted to cause the blister strip 20 to advance before and/or during and/or after each actuation of the device. The second displacement means 45 are adapted to displace the reservoir 21 to be emptied against said perforator and/or cutter means 30 during actuation. The second displacement means 45 can be urged by a resilient element, such as a spring or any other equivalent resilient element, said resilient element being suitable for being prestressed while the device is being opened. The first displacement means 40 preferably comprise an indexer wheel 40 that receives and guides the blisters. Turning the wheel 40 causes the blister strip 20 to advance. In a particular angular position, a given reservoir 21 is always in a position facing the opening means 30. The second displacement means 45 can include a rotary support element that turns about an axis of rotation 45', said indexer wheel 40 being rotatably mounted on said support element.

An actuation cycle of the device can be as follows. While the device is being opened, the two cap-forming lateral portions are moved apart by pivoting on the body in order to open the device and thus load the device. In this position, the indexer wheel 40 cannot be displaced towards the needle 30, since the second displacement means 45 are held by appropriate blocking means. Preferably, it is while the user is inhaling through the mouthpiece 1 that the blocking means are unblocked, thereby causing said support element 45 to pivot and thus said indexer wheel 40 to move towards the needle 30, and thereby causing a reservoir 21 to be opened.

In the embodiments shown, the reservoir 21 is displaced towards its open position so as to be opened by the needle 30 that does not move relative to the body 10. However, it can be envisaged that the needle can also be movable during the stage of opening the reservoir 21. For example, the needle could be displaced towards the reservoir 21 while the reservoir 21 is displaced towards the needle. In another variant, it is also possible to envisage that the reservoir 21 and the needle are displaced in the same direction during actuation, the reservoir 21 being displaced quicker in said direction, such that it comes into contact with the needle so as to be opened.

As explained above, it is desirable for the opening means to be actuated by the user inhaling. In order to trigger the reservoir opening means by inhalation, an inhalation trigger system is provided that advantageously comprises a unit 60 that is displaceable and/or deformable under the effect of inhalation, the unit 60 being adapted to release the blocking means. The unit 60 advantageously comprises a deformable air-chamber. Inhalation by the user causes said deformable air-chamber to deform, thereby making it possible to release said blocking means and to enable the displacement of the second displacement means 45, and therefore of a respective reservoir 21 towards its opening position. The reservoir 21 is therefore opened only on inhalation, such that it is emptied simultaneously. Thus, there is no risk of any of the dose being lost between opening the reservoir and emptying it.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

The inhaler further includes a dispenser chamber 70 for receiving the dose of powder after a respective reservoir 21 has been opened. The dispenser chamber 70 is advantageously provided with at least one bead 75 that is displaced inside said chamber 70 during inhalation so as to improve dispensing of the air and powder mixture after a reservoir 21 has been opened, in order to increase the effectiveness of the device.

It can be advantageous for the opening means 30, in particular the needle, to be formed directly on said dispenser chamber 70, e.g. at the end of a channel 69 leading to said chamber 70.

After inhalation, when the user closes the device, all of the components return to their initial, rest position. The device is thus ready for a new utilization cycle.

In an advantageous aspect of the inhaler, the individual reservoirs or blisters 21 are formed on an elongate strip 20 that, initially, is mainly stored in the form of a roll in a storage housing inside the body 10 of the device. Advantageously, the rolled-up blister strip 20 is held by inner walls of said storage housing without its rear end 28 (rear in the advancement direction of the blister strip 20) being fastened relative to said body 10, thereby enabling the blister-strip roll to be assembled more easily inside the device. The blister strip 20 is displaced by the user, advantageously by means of the indexer wheel 40 that advantageously presents at least one and preferably more recesses 41 having a shape that corresponds to the shape of the blisters. Thus, when the indexer wheel 40 turns, it causes the blister strip 20 to advance. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes.

After opening one or more blisters, the blister-strip portion with the empty reservoirs must be suitable for being stored in easy and compact manner in the device, while avoiding any risk of blockage. Advantageously, the used blister strip is rolled-up automatically, once again forming a roll.

In the invention, the leading end 25 of the blister strip 20 is fastened to a receiver element 50. The receiver element 50 is displaceable along a path that is defined by guide means 100, e.g. a slot. In a variant, the guide means could also be made in some other way, e.g. by projections, ribs, rails, or the like. The slot 100 can advantageously be substantially rectilinear, as shown in the figures, but, in a variant, it could also be of some other shape, depending on the shape of the reception space in which the leading portion of the strip 20 that supports the empty blisters is rolled up. Advantageously, the receiver element 50 is displaced progressively along said slot each time the device is actuated, and as the strip 20 is rolled up around it. This embodiment makes it possible to optimize the place allocated to the used strip portion between a starting position (FIG. 2) in which the receiver element is at the outer edge of the reception portion, and a final position in which the receiver element is displaced approximately to the center of the reception portion. Thus, as the strip with the full blisters is unrolled, and as the strip with the empty blisters is rolled up, the receiver element 50 is displaced along said slot 100. Advantageously, the displacement is achieved merely by the thrust that is exerted against the walls of the reception portion by the strip rolling up on the receiver element 50. In a variant, thrust means, such as a spring, could be envisaged for displacing the receiver element 50 in the slot 100.

Preferably, the receiver element 50 is also rotatably mounted, advantageously on a support surface 57. The support surface 57 is preferably movable under the effect of second displacement means 45, i.e. the receiver element 50 is displaced with the reservoir to be emptied on each actuation. In the embodiment shown, it is the cassette receiving the strip 20, the indexer wheel 40, and the support surface 57 that pivot as a unit about the pivot axis 45'. To ensure that the leading portion of the blister strip 20, namely the portion including the empty blisters, is rolled up properly in the reception portion, the rotary receiver element 50 is preferably adapted to exert a traction force on the strip 20, in particular on its leading end 25. Thus, any risk is avoided of the strip being rolled up poorly, e.g. folding up concertina-like, etc., which would risk blocking the device. The traction force can be exerted by a spring 500 that urges said receiver element 50 to turn and thus pulls on the strip. In particular, the spring may be a spiral spring, a leaf spring, or a helical spring.

Figure 2:
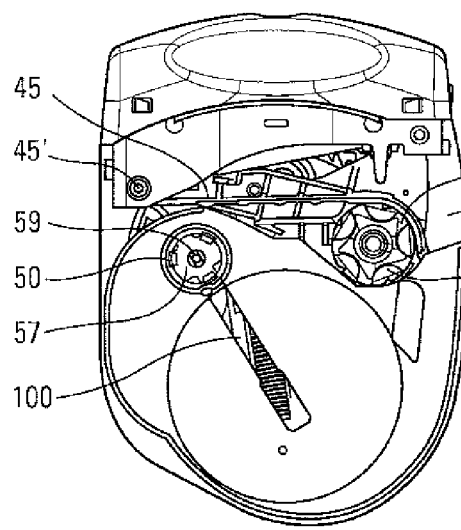
FIG. 2 is a view in partial section of the FIG. 1 device, at the beginning of use.
Figure 3:
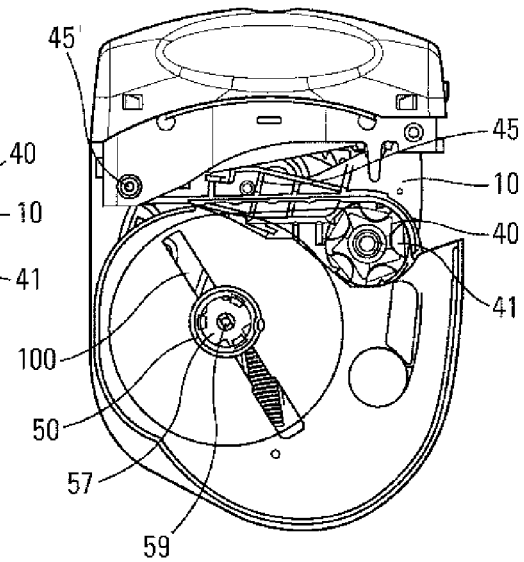
FIG. 3 is a view similar to the view in FIG. 2, after several uses.

FIGS. 1 to 3 show an advantageous variant embodiment, in which the receiver element 50 forms a cylinder that is rotatably mounted about a fastener pin 59 that cannot turn, and to which there is fastened a portion, preferably an end portion, of the spring 500. Thus, in this embodiment, the spring 500 is disposed around said fastener pin 59, inside said cylinder forming the receiver element 50.

The spring 500 is stressed before first use or during assembly, and naturally, the maximum traction force exerted on the strip 20 is insufficient to tear, deform, or displace the strip 20 in the absence of actuation. Progressively, on each actuation, the spring relaxes, causing the receiver element 50 to turn, while, simultaneously, said receiver element is displaced in translation along the slot 100. The characteristics of the spring 500 are preferably selected such that it exerts a traction force until the last doses, but in certain applications, it may be sufficient for the traction force to be exerted only at the start of use, so as to guarantee a proper start of rolling-up for the strip portion with the empty reservoirs.

Preferably, the receiver element 50 is fastened on the support surface 57, in particular snap-fastened, such that it can be displaced only in turning, but neither laterally (or transversally), nor vertically (or axially). Advantageously, snap-fastening can be performed by means of snap-fastener studs so as to limit friction during turning. In this configuration, it is the support surface 57 that co-operates with the guide means, and in particular that slides along the slot 100 in the embodiment shown.

The traction force exerted by the rotary element 50 on the strip 20 is completely independent of the first displacement means, namely the indexer wheel 40 that causes the strip to advance during each actuation. This makes it possible to guarantee that the traction force does not depend on the diameter of the rolled-up used blister strip, as would occur if the turning of the rotary receiver element 50 was correlated to the turning of the indexer wheel 40. It is also completely independent of the second displacement means 45, such that the invention avoids providing actuator means that are relatively complex in order to create traction force on the strip during actuation of the inhaler. This simplifies manufacture and assembly of the inhaler.

Advantageously, the reception portion may include guide walls, in particular an external guide wall that is curved, e.g. cylindrical, and against which the blister strip 20 slides. An internal guide wall may also be provided at the inlet to the reception portion, and preferably extends approximately parallel to the external guide wall, so as to form a guide channel for the blister strip 20. The guide walls further facilitate proper rolling up of the blister strip 20 around the receiver element 50, and progressive displacement of said receiver element along the slot 100.

The present invention therefore makes it possible to provide a dry-powder inhaler that performs the following functions:

- a plurality of individual doses of powder stored in individual sealed reservoirs, e.g. 30 or 60 doses stored on a rolled-up strip;
- the powder is released by perforation that is achieved by the user inhaling, the blister being perforated by means of an inhalation detector system that is coupled to a pre-stressed release system;
- appropriately-shaped drive means that are engaged with blisters so as to displace the blister strip on each actuation, and to bring a new reservoir into a position in which it is to be opened by appropriate opening means;
- safe and reliable storage of the used portion of the strip, by being rolled up around an element that is displaceable both in rotation and in translation, and that is preferably adapted to pull on the strip on each actuation, the traction being completely independent of the first displacement means, namely the indexer wheel 40 that is used to cause the blister strip 20 to advance.

Other functions are also provided by the device of the invention as described above. It should be observed that the various functions, even if they are shown as being provided simultaneously on the various embodiments of the inhaler, could be implemented separately. In particular, the inhalation trigger mechanism could be used regardless of the type of reservoir opening means, regardless of the use of a dose indicator, regardless of the way in which the individual reservoirs are arranged relative to one another, etc. The cocking means and the inhalation trigger system could be made in some other way. The same applies for other component parts of the device.

Various modifications can also be envisaged by a person skilled in the art, without going beyond the ambit of the present invention, as defined by the accompanying claims.

The invention claimed is:

1. A fluid dispenser device comprising: a body; an elongate flexible strip supporting a plurality of reservoirs each containing a dose of fluid or powder; reservoir-opening means for opening a respective one of the plurality of reservoirs on each actuation; first displacement means for causing said elongate flexible strip to advance before or during or after each actuation, so as to bring at least one of the plurality of reservoirs into register with said reservoir-opening means; and second displacement means for displacing a full at least one of the plurality of reservoirs against said reservoir-opening means each time the fluid dispenser device is actuated, a leading end of said elongate flexible strip, in an advance direction of said elongate flexible strip, being fastened to a receiver element, said fluid dispenser device being characterized in that said receiver element is displaceable, on a path along guide means, between a first position that corresponds to a first actuation of the fluid dispenser device and a second position that corresponds to a last actuation of the fluid dispenser device.

2. A fluid dispenser device according to claim 1, wherein said receiver element is also rotatably mounted.

3. A fluid dispenser device according to claim 2, wherein said receiver element is fastened to a stressed spring that is adapted to exert a force on said receiver element so as to urge said receiver element to turn, such that said receiver element exerts a traction force on said elongate flexible strip, said traction force being independent of said first and second displacement means.

4. A fluid dispenser device according to claim 3, wherein said traction force is at a maximum when the fluid dispenser device is first used and reduces on each actuation as the stressed spring relaxes.

5. A fluid dispenser device according to claim 3, wherein said stressed spring is a spiral spring, a leaf spring, or a helical spring.

6. A fluid dispenser device according to claim 3, wherein said stressed spring is fastened firstly to a fastener pin that cannot turn, and secondly to said receiver element.

7. A fluid dispenser device according to claim 1, wherein said guide means include a slot in which the receiver element can slide.

8. A fluid dispenser device according to claim 1, wherein said guide means are substantially rectilinear.

9. A fluid dispenser device according to claim 1, wherein said receiver element is displaced along said guide means each time the fluid dispenser device is actuated.

10. A fluid dispenser device according to claim 1, wherein said receiver element is mounted on a support surface, so as to fasten said receiver element both axially and transversally relative to said support surface, while enabling said receiver element to turn about an axis of rotation, said support surface sliding along said guide means.

11. A fluid dispenser device according to claim 1, wherein said receiver element is rotatably fastened on a support surface that is secured to said second displacement means, said support surface being displaced in rotation each time the fluid dispenser device is actuated, together with at least one of the plurality of reservoirs to be opened.

12. A fluid dispenser device according to claim 1, wherein said reservoir opening means comprise a needle that does not move relative to said body, at least one of the plurality of reservoirs being displaced against said needle each time the fluid dispenser device is actuated, said needle penetrating into at least one of the plurality of reservoirs so as to empty at least one of the plurality of reservoirs by means of an inhalation flow.

13. A fluid dispenser device according to claim 12, wherein said reservoir opening means are adapted to be controlled by a user inhaling, such that at least one of the plurality of reservoirs is opened and emptied simultaneously by said inhalation flow.

14. The fluid dispenser device according to claim 10, wherein said receiver element is mounted on the support surface by a snap-fastener stud.

15. A fluid dispenser device comprising: a body; an elongate flexible strip supporting a plurality of reservoirs, each of the plurality of reservoirs containing a dose of fluid or powder; a perforator configured to open a respective one of the plurality of reservoirs on each actuation; an indexer wheel that indexes the elongate flexible strip in an advance direction so as to bring one of the plurality of reservoirs into register with the perforator; and a rotary support element that displaces a respective one of the plurality of reservoirs that is brought into register with the perforator against the perforator each time the fluid dispenser device is actuated, a leading end of the elongate flexible strip, in an advance direction of the elongate flexible strip, being fastened to a receiver element; wherein the receiver element is displaceable, on a path along a guide, between a first position that corresponds to a first actuation of the fluid dispenser device and a second position that corresponds to a last actuation of the fluid dispenser device.

16. The fluid dispenser device according to claim 15, wherein the receiver element is rotatably mounted.

17. The fluid dispenser device according to claim 16, wherein the receiver element is fastened to a stressed spring configured to exert a force on the receiver element so as to urge the receiver element to turn, such that the receiver element exerts a traction force on the elongate flexible strip, the traction force being independent of the indexer wheel and the rotary support element.

18. The fluid dispenser device according to claim 15, wherein the guide is a slot in which the receiver element is configured to slide.

19. The fluid dispenser device according to claim 15, wherein the receiver element is rotatably fastened on a support surface that is secured to the rotary support element, the support surface being displaced in rotation each time the fluid dispenser device is actuated, together with the respective one of the plurality of reservoirs to be opened.

20. The fluid dispenser device according to claim 15, configured such that opening of the respective one of the plurality of reservoirs is adapted to be controlled by a user inhaling, such that the respective one of the plurality of reservoirs is opened and emptied simultaneously by an inhalation flow.

\* \* \* \* \*